United States Patent [19]

Relyveld et al.

[11] Patent Number: 4,552,756

[45] Date of Patent: Nov. 12, 1985

[54] ALLERGENIC COMPOSITIONS

[75] Inventors: Edgar H. Relyveld; Emile Henocq, both of Paris, France

[73] Assignee: Institut Pasteur, Paris, France

[21] Appl. No.: 392,594

[22] Filed: Jun. 28, 1982

Related U.S. Application Data

[62] Division of Ser. No. 194,577, Oct. 6, 1980, Pat. No. 4,350,680.

[30] Foreign Application Priority Data

Oct. 8, 1979 [FR] France .................................. 7924948

[51] Int. Cl.$^4$ ............................................. A61K 39/00
[52] U.S. Cl. ........................................ 424/88; 424/91
[58] Field of Search ..................................... 424/88, 91

[56] References Cited

PUBLICATIONS

Rose et al–Condensed Chemical Dictionary, 7th edit. (Reinhold Pub., N.Y.) p. 372.
King et al–Biochemistry, vol. 3, No. 3 (Mar. 1964) pp. 458–463.
King et al–Biochemistry, vol. 1, No. 4 (Jul. 1962) pp. 709–720.
Johnson et al–Chem. Abst., vol. 63 (1965) p. 10487b.
Kabasawa et al–Chem. Abst. vol. 90 (1979) p. 202,058u.
Smart et al–Chem. Abst., vol. 93 (1980) pp. 24,105j.
Smart et al–Int. Arch. Allergy Appl. Immunol., vol. 62 (1980) pp. 179–187.

*Primary Examiner*—Sam Rosen
*Attorney, Agent, or Firm*—Toren, McGeady, Stanger, Goldberg & Kiel

[57] ABSTRACT

Improvement in the preparation of allergens, for the obtention of more stable and more effective preparations from extracts of various materials such as pollens, house dust, kapok, wool, molds, etc. extracts containing only allergenic substances having molecular weights in the range of from about 10,000 and 50,000 and being free from enzymes are broadly contemplated.

The substances have no allergenic activity are removed from the aqueous extract. In particular, molecular masses below 14,000 and above 45,000 are eliminated.

The allergen thus improved is suitable in the adsorbed form, for example, on alumina and phosphates of aluminum or of calcium; it provides particularly good results when the adsorbent is a special phosphate in which the ponderal ratio Ca/P is 1.55 to 1.90.

10 Claims, 2 Drawing Figures

ALLERGENIC COMPOSITIONS

This is a division of application Ser. No. 194,577, filed Oct. 6, 1980, now U.S. Pat. No. 4,350,686.

BACKGROUND OF THE INVENTION

1. Field of the Invention

The invention relates to the preparation of allergens, to which it imparts an improvement permitting the obtention of improved allergenic compositions; the latter also form part of the invention.

2. Description of the Prior Art

Allergology has assumed an important position in therapy in recent decades, and its role is expanding; not only does it detect the allergic character in various old diseases, but it is also called on to remedy attacks of this type which are multiplied by modern pollution. Likewise there is always a need for good hyposensitizing agents, in spite of the presence on the market of well-known allergens extracted from various materials, such as: pollens, flours, house dusts, hair, kapok, feathers, molds, etc. Although a number of preparations, particularly retard-allergens adsorbed on mineral supports such as gels with an alumina base, for example, yield excellent results, the inocuity and constancy of activity of some of them leave something to be desired. The duration of use of several allergenic extracts available at the present time, is therefore limited in time.

SUMMARY OF THE INVENTION

The present invention confers an improvement making it possible to obtain much more stable and more active allergens which provoke no secondary reactions in the organism in which they are injected. The improved allergens produced according to this invention have a considerably longer useful life and they lend themselves particularly well to the preparation of the form adsorbed on a mineral gel.

The invention results from the discovery of a phenomenon, heretofore unknown in this field; the presence of various enzymes in the allergenic extracts was not considered as unfavorable, and it was even proposed to profit by it in classifying or appreciating their activity (GLEIGH G. J. et coll, "Allergy and Clinical Immunology"- Excerpts Medical, Amsterdam, 1977, pages 184 and 213); but the Institut Pasteur has found that at least some of these enzymes degraded constituent proteins of the allergens. Thus, unexpectedly, the Applicants have determined the cause of the instability of the allergenic extracts; they also found that the enzymes, responsible for the attack on the useful proteins, as well as other impurities, interfere with the adsorption of allergens on mineral adjuvants. In addition, these, or some of these enzymes can be the cause of the production of antibodies, by a reaction of the organism against the impurities which they constitute in the allergen injected.

The improved method, according to the invention, therefore comprises the elimination of the enzymes present, from the aqueous extract of an allergen, as soon as possible after the preparation of this extract. It is a question, as a matter of fact, of allowing the least possible time for the attack on the useful proteins by the proteases of the medium present.

Thus the process according to the invention, which comprises the preparation of an aqueous extract of allergen, is characterized by the elimination, from this extract, of substances not having the desired allergenic activity. In a particular form of execution, the solution is allowed to retain only the allergenically active substances whose molecular masses range from about 10,000 to 50,000, and particularly from 14,000 to 45,000 (by precipitation).

DESCRIPTION OF THE PREFERRED EMBODIMENT

Figure 1:
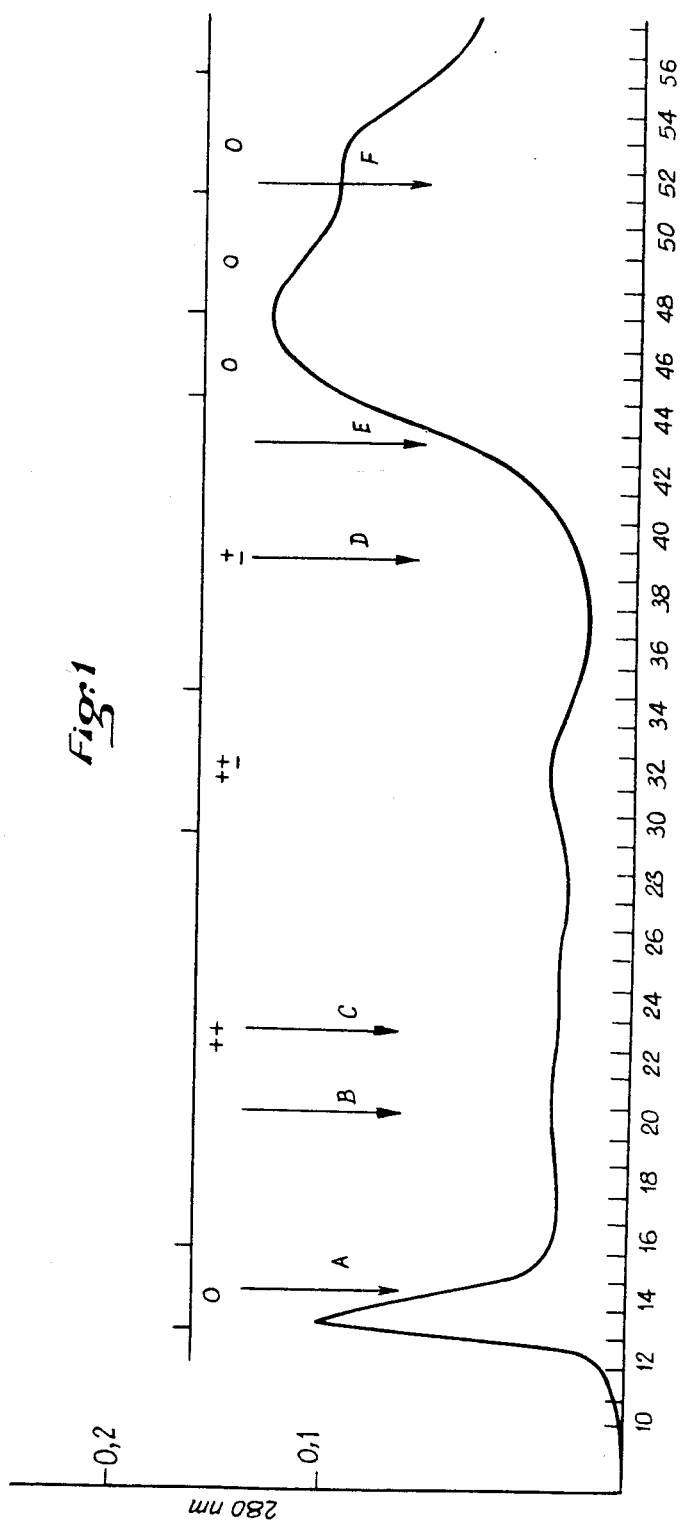

In the practice of the invention, it is, moreover, desirable to carry out the abovementioned operation on an extract already freed of various other impurities: this is done in known fashion, by the precipitation and redissolution of the proteins in the extract.

The elimination of the inactive fractions, particularly those whose molecular masses are below 10,000 or 14,000, and above 55,000 or 45,000, according to the invention, can be embodied by any appropriate means, well known in the art, for example, chromatographic methods, fractional precipitations, electrophoresis, etc. Filtration on gel, in this manner of working, renders valuable service, and there is a description below, by way of non-limiting example, of the fractioning of a pollen extract by molecular screening.

The methods of extraction of protein from various materials, in particular with a view to the preparation of allergenic compositions, are known, and there is no need to describe them here. By way of example, however, an operational method will be discussed, which is particularly suitable and which has been the subject of publications such as French Pat. No. 1,604,135. This method consists in treating 100 g of material, particularly pollens, with 1 liter of a solution of $Na_2HPO_4.12H_2O$ at 25 g/l, containing 1/10,000 of merthiolate. After 24 hours of agitation of +4 degC., the solution is separated from the solid by centrifuging. The crude extract thus obtained is purified by saline precipitation, which consists in adding 604 g of crystallized ammonium sulfate to 1 liter of this extract, and leaving it in contact, with agitation, for 3 h at +4 degC. The precipitate formed is then separated by centrifuging and redissolved in a solution of disodium phosphate at 25 g/l containing 1/10,000 of merthiolate. The solution obtained is dialyzed against a fresh solution of disodium phosphate at 25 g/l, again supplemented by merthiolate.

It is on an extract, that is to say a solution prepared as indicated above, from phleum pollen, that the operations brought to light in the remainder of the present description were carried out.

This solution is first subjected to a fractioning by molecular screening. To do so, a chromatographic column, 35 mm in diameter and 560 mm high is used; it is charged with Sephadex G-100, whose range of possible fractioning extends over the molecular masses of 4,000 to 150,000. The fractioning is conducted with an eluent constituted by a solution of disodium phosphate at 25 g of $Na_2HPO_4.12H_2O$ per liter, containing 0.9% of NaCl and 1/10,000 of merthiolate. The operation is conducted on 5 ml portions of extract, each of them being followed by a passage through the elution buffer. Fractions of 10 ml are collected, on which are determined:

The molecular mass of the dissolved substance,
The presence of enzymes, and
The reaction on the skin.

Furthermore, a similar fractioning, and the abovementioned determinations are made on an extract of phleum pollen in disodium phosphate, of the same concentration, but no yet purified by precipitation in ammonium sulphate: this solution is called crude extract in the remainder of the description.

The results of these tests are reported in the attached tables and graphs.

FIG. 1 shows the curve of elution of the crude extract of phleum pollen: the numbers of the fractions of 10 ml are plotted in the abscissa, while the ordinate indicates the absorbance at 280 nm. At the top of the graph, on a line parallel to the abscissa, are the reactions on the skin of the fractions mixed, from the 13th to the 55th fraction. Letters A to F designate the reference marks of substances with known molecular masses:

A—Dextran blue mol. mass. 2,000,000
B—Albumin mol. mass. 65,000
C—Egg albumin mol. mass. 45,000
D—Lysozyme mol. mass. 14,600
E—Bacitracine mol. mass 1,450
F—DNP ethanolamine mol. mass. 227

The reaction on the skin is determined by the known "prick" method, which consists in placing a drop of liquid on the skin and pricking through this drop with a needle; after 20 minutes approximately, an allergic subject presents a positive reaction, noted +, that is to say a papule and an erythema. A single + signifies that the papule extends over an average diameter of 5 mm; the number of +'s indicates the multiples of 5 mm observed.

In the case of the curde extract in FIG. 1, a skin reaction is noted for the combined fractions no. 16 to 29 (++), 30 to 34 (+±) and 35 to 44 (±): there is no reaction before fraction 15 nor after fraction 45, which signifies that outside of fractions 16 to 44 there is no longer a product of any interest as an allergen. The useful range therefore ranges from no. 16 to no. 44.

Figure 2:
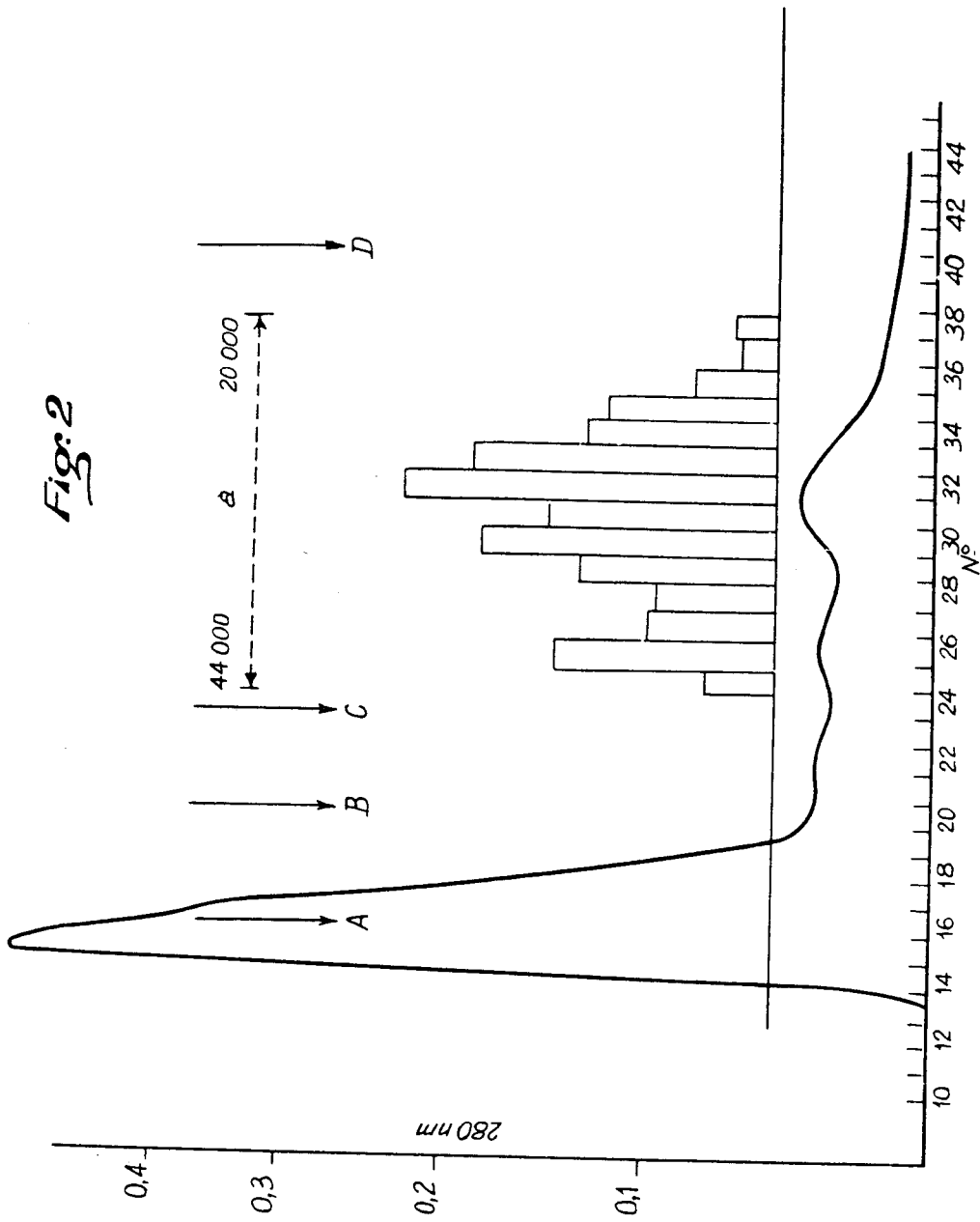

FIG. 2 shows the elution diagram, analogous to that in FIG. 1, but applied to the extract of phleum pollen previously purified by precipitation in ammonium sulfate and redissolution in a solution of disodium phosphate; it is therefore the proteins almost exclusively, which are thus subjected to the separation by molecular screening. On this graph, the series of vertical rectangles represents the only fractions of interest, yielding reactions of + to +++ on the skin of allergic subjects, determined by the prick method. The heights of the rectangles are proportional to the diameter of the papules formed on the skin: 25 mm of this height corresponds to 5 mm of papule diameter. The useful range comprises fractions no. 25 to 38, corresponding essentially to molecular masses of 44,000 to 20,000. Here again are the indications provided by the crude extract in FIG. 1, but with a contraction of the useful range.

According to the invention, in the present case, given by way of example, only fractions no. 25 to 38 are collected for preparation of the allergenic composition, while the other fractions are discarded, in contrast to previous practice.

The proof that the adopted fractions 25 to 38 contain practically no enzymes is provided by measurements made by the very practical method known as the "API ZYM" system. This method consists in introducing, into a series of 20 cupels, the bottom of which is constituted by a support containing the enzymatic substrate with its buffer, of a small amount of liquid to be studied, and, after incubation, in reacting this liquid with two reagents, tris (hydroxy-methyl)amino-methane and rapid blue BB. The presence of enzymes manifests itself by the coloration appearing in the cupels, which is rated on a scale of 1 to 5, the latter figure corresponding to maximum intensity. With the aid of this system, certain authors have been able to find the presence of numerous enzymes in extracts of graminaceous pollen; thus, Jean Bousquet et col, made measurements (Annals of Allergy, vol. 41, September 1978, p. 164–169)concerning a whole series of enzymes such as phosphatases, esterases, lipases, leucine-amino-peptidase, valine-amino-peptidase, trypsin, chymotrypsin, beta-glucose-aminidase, glucosidases, etc.

By applying the API ZYM system to the products in FIG. 1 and 2, described above, the results given in table 1 below were found. This table presents, for the cupels in the API system, the rating (from 0 to 5) determined by comparison of the colored scale of the system with the shade developed in the cupel. The letters "tr" stand for "trace." The tests are, of course, accompanied by a control sample formed by a solution of disodium phosphate at 25 g/l containing merthiolate, and a heated extract of pollen.

The result of the data in table 1 is that the crude extract definitely contains enzymes and that the content thereof is somewhat diminished owing to the purification in ammonium sulphate. The enzymes disappear almost completely following the fractioning by filtration on gel; practically none remain beyond the 22nd fraction; but, there are some in fractions 14 to 18 which lack allergenic activity. (See table 1)

It was mentioned above that the elimination of the components of molecular masses below 14,000 and above 45,000 also improve the adsorption of the allergen by mineral gels. Thus it can be noted that the useful fractions, separated according to FIG. 2, are adsorbed better on known adsorbents, such as for example, alumina, phosphate of alumina or phosphate of calcium. The adsorption is particularly effective for the special phosphate in which the ponderal ratio Ca/P is comprised between 1.55 and 1.90, as described in French Pat. No. 72,12036 (publication 2.181.426 of 12/7/73).

Such a gel is prepared, in particular, by mixing a solution of 25 g of disodium phosphate in 1 liter of water, with 2/10,000 of merthiolate supplemented by 20 ml of allergenic extract, prepared from 100 g of pollen, as indicated at the start of the present description. To the mixture obtained, 1 liter of water, containing 10.2 g of $CaCl_2.2H_2O$ is added. This addition is made very rapidly under agitation, and the pH of the medium is brought to 6.8–7 by means of normal soda.

In a first series of tests, the prick method mentioned above was used to determine the reaction on the skin of 11 patients. For each of them, an extract of phleum, purified by precipitation in ammonium sulfate was used, plus - furthermore - the liquid supranatant after precipitation of the special calcium phosphate in the presence of the same extract, as just indicated. In both cases, the dilution of the extract is 1/1000. The results are again indicated by means of +'s, each of which corresponds to 5 mm of papule formed on the skin of the patient. (See table 2).

It is clear that the adsorption was very effective, since the overall diminution of the reaction on the skin was $$((22-8.5)/22) = 61.4\%$$

Similar tests were run with the same special calcium phosphate, no longer mixed with the total phleum extract, but with the enzymeless fractions, represented and described in regard to FIG. 2. The reactions on the skin were determined at dilutions ranging from 1/1,000 to 1/1,000,000, table 3 shows the results thereof, compared on the one hand for the extract, that is to say the fractions themselves, and on the other hand, on the liquid supranatant after the precipitation of the phosphate. For the dilution of 1/1,000, the reaction is determined by the prick method, while the intradermal reaction is used for the other dilutions. (see table 3)

It is seen that the adsorption of the fractioned phleum extract is very extensive.

Similar results are obtained with extracts obtained from other pollens, in particular those of rye, cockle, dactylis, etc.

Table 1 (see original text)

A. Sample B. Concentration C. Numbers of cupels
  1. Control
  2. Total crude extract (FIG. 1)
  3. Total extract purified in $NH_4$ sulf. (FIG. 2)
  4. 4 Ditto, fractions 14 to 18 (etc.)

Table 2 (see original text)

A. Patient No.
  1. Extract
  2. Supranatant

Table 3 Dilutions (see original text)

A. Patient No. B. Liquid extract c. Supranatant

TABLE 1

| Sample | Concentration | Number of Cupels | | | | | | | | | | | | | | | | | | |
|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 |
| Control | | | | tr | tr | | | | | | | | tr | | | | | | | | |
| Total crude extract (FIG. 1) | 1/100 | | 5 | ~5 | 3 | tr | 4 | 3 | 3 | 3 | tr | >5 | >5 | 2 | | | | | 3 | 1 |
| Total extract purified in $NH_4$ sulf. (FIG. 2) | 1/100 | | 4 | 3 | 2 | | 3 | 1 | | | | 5 | 5 | | | | | | | 1 |
| dtto.fractions 14 a 18 | 1/34.5 | ≦1 | | 3 | 1 | | 3 | | | | | 5 | 4 | | | | | | | tr |
| dtto.fraction 15 | 1/100 | | | 1 | tr | | | | | | | 5 | 2 | | | | | | | tr |
| dtto.fraction 22 | 1/100 | | | 1 | tr | | | | | | | 1 | 1 | | | | | | | |
| dtto.fraction 24 | 1/100 | | | 0.5 | tr | | | | | | | tr | 1 | | | | | | | |
| dtto.fraction 26 | 1/100 | | | tr | tr | | | | | | | | 1 | | | | | | | |
| dtto.fraction 29 | 1/100 | | | tr | tr | | | | | | | | 1 | | | | | | | |
| dtto.fraction 31 | 1/100 | | | tr | tr | | | | | | | | 1 | | | | | | | |
| dtto.fraction 31 | 1/7 | | | 1 | ≦1 | | | | | | | | tr | | | | | | | |
| dtto.fraction 51 | 1/100 | | | tr | tr | | | | | | | | 1 | | | | | | | |
| dtto.fraction 56 | 1/100 | | | tr | tr | | | | | | | | 1 | | | | | | | |

TABLE 2

| | No. patient | | | | | | | | | | | |
|---|---|---|---|---|---|---|---|---|---|---|---|---|
| | 1 | 2 | 3 | 4 | 5 | 6 | 7 | 8 | 9 | 10 | 11 | Total |
| Extract | ++ | + | +++ | +± | +++ | +± | + | ++++ | + | ++ | ++ | 22 |
| Supernatant | + | 0 | + | ± | ++ | ± | ± | + | 0 | +± | ± | 8.5 |

TABLE 3

| Patient No. | DILUTIONS | | | | | | | |
|---|---|---|---|---|---|---|---|---|
| | Liquid Extract | | | | Supernatant | | | |
| | $1/10^6$ | $1/10^5$ | $1/10^4$ | $1/10^3$ | $1/10^6$ | $1/10^5$ | $1/10^4$ | $1/10^3$ |
| 1 | +± | ++ | | | ± | ± | | |
| 2 | | | | ++ | | | | + |
| 3 | ± | + | ++± | | 0 | 0 | +± | |
| 4 | +++ | ++++ | | | + | +± | | |
| 5 | + | + | +± | 0 | 0 | 0 | 0 | 0 |
| 6 | 0 | 0 | | 0 | 0 | 0 | | 0 |
| 7 | ++ | +++ | | + | 0 | 0 | | + |
| 8 | ++ | | | ± | + | | | ± |
| 9 | ± | ++± | +++ | 0 | 0 | + | ++ | 0 |
| 10 | + | ++± | | 0 | ± | ± | | 0 |
| 11 | | | | + | | | | 0 |
| 12 | +± | +± | | ± | ± | ± | | 0 |
| 13 | +± | ++ | | + | ± | ± | | 0 |
| 14 | + | ++ | | 0 | + | ± | | 0 |
| Total | 15.5 | 21.5 | 7 | 6 | 5 | 5 | 3.5 | 2.5 |
| Diminution | | | | | 67.7 | 76.7 | 50 | 58.3 |

TABLE 3-continued

| Patient No. | DILUTIONS | | | | | | | |
|---|---|---|---|---|---|---|---|---|
| | Liquid Extract | | | | Supernatant | | | |
| | $1/10^6$ | $1/10^5$ | $1/10^4$ | $1/10^3$ | $1/10^6$ | $1/10^5$ | $1/10^4$ | $1/10^3$ |
| % | | | | | | | | |

We claim:

1. An allergenic composition for hyposensitizing allergic patients by intracutaneous administration of the composition to the patients, comprising an aqueous extract of pollen, flour, house dust, kapok, wool or molds which contains only the allergenically active substances having molecular weights in the range of from about 10,000 and 50,000, and being free from enzymes.

2. The composition according to claim 1 wherein the allergenically active substances of said extract have molecular weights ranging between 14,000 and 45,000.

3. The composition according to claim 1 wherein the allergenically active substances of said extract have molecular weights ranging between 20,000 and 44,000.

4. The composition according to claim 1 which contains an aqueous gel of a mineral compound having adsorbed said allergenically active substances.

5. The composition according to claim 4 wherein said aqueous gel is selected from the group consisting of alumina gel, aluminum phosphate gel and calcium phosphate gel.

6. The composition according to claim 5 wherein said calcium phosphate gel has a ponderal ratio of calcium to phosphorus, Ca/P, of 1.55 to 1.90.

7. The composition according to claim 2 which contains an aqueous gel of calcium phosphate having adsorbed said allergenically active substances, the ponderal ratio Ca/P in the phosphate being 1.55 to 1.90.

8. The composition of claim 7, wherein said ratio Ca/P is 1.62 to 1.85.

9. The composition according to claim 3 which contains an aqueous gel of calcium phosphate having adsorbed said allergenically active substances, the ponderal ratio Ca/P in the phosphate being 1.55 to 1.90.

10. The composition according to claim 9 in which said ratio Ca/P is 1.62 to 1.85.

* * * * *